US012390195B2

(12) United States Patent
Yonemori et al.

(10) Patent No.: US 12,390,195 B2
(45) Date of Patent: Aug. 19, 2025

(54) ULTRASOUND DIAGNOSIS APPARATUS AND IMAGE PROCESSING APPARATUS

(71) Applicant: CANON MEDICAL SYSTEMS CORPORATION, Tochigi (JP)

(72) Inventors: Keita Yonemori, Utsunomiya (JP); Yasunori Honjo, Utsunomiya (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 173 days.

(21) Appl. No.: 17/663,939

(22) Filed: May 18, 2022

(65) Prior Publication Data

US 2022/0273266 A1 Sep. 1, 2022

Related U.S. Application Data

(63) Continuation of application No. PCT/JP2021/019988, filed on May 26, 2021.

(30) Foreign Application Priority Data

May 26, 2020 (JP) ................. 2020-091532
May 26, 2021 (JP) ................. 2021-088405

(51) Int. Cl.
*A61B 8/00* (2006.01)
*A61B 8/06* (2006.01)
*G06F 3/04845* (2022.01)

(52) U.S. Cl.
CPC ............... *A61B 8/463* (2013.01); *A61B 8/06* (2013.01); *A61B 8/469* (2013.01); *A61B 8/485* (2013.01); *G06F 3/04845* (2013.01); *G06F 2203/04803* (2013.01)

(58) Field of Classification Search
CPC .......... A61B 8/463; A61B 8/469; A61B 8/485
See application file for complete search history.

(56) References Cited

U.S. PATENT DOCUMENTS

| 6,419,632 | B1 | 7/2002 | Shiki et al. |
| 2005/0238218 | A1 | 10/2005 | Nakamura |
| 2012/0133663 | A1 | 5/2012 | Tanigawa |
| 2012/0330158 | A1 | 12/2012 | Sawayama et al. |
| 2015/0087980 | A1 | 3/2015 | Yao et al. |

(Continued)

FOREIGN PATENT DOCUMENTS

| CN | 103619245 A | 3/2014 |
| CN | 103648398 A | 3/2014 |

(Continued)

OTHER PUBLICATIONS

International Search Report issued Aug. 10, 2021 in PCT/JP2021/019988 filed on May 26, 2021, 2 pages.

(Continued)

*Primary Examiner* — Joel F Brutus
(74) *Attorney, Agent, or Firm* — Oblon, McClelland, Maier & Neustadt, L.L.P.

(57) ABSTRACT

An ultrasound diagnosis apparatus according to an embodiment includes processing circuitry. The processing circuitry causes plural images to be displayed in plural second display regions that have been arranged, the plural images being obtained by an ultrasound scan or ultrasound scans and corresponding to a region of interest in a morphology image displayed in a first display region.

19 Claims, 9 Drawing Sheets

(56) References Cited

U.S. PATENT DOCUMENTS

| | | |
|---|---|---|
| 2015/0164480 A1 | 6/2015 | Watanabe et al. |
| 2015/0320395 A1 | 11/2015 | Sato |
| 2016/0275709 A1 | 9/2016 | Gotman et al. |
| 2017/0055956 A1* | 3/2017 | Osumi ............... A61B 8/06 |
| 2017/0150948 A1 | 6/2017 | Kanayama |
| 2017/0156700 A1 | 6/2017 | Honjo et al. |
| 2018/0008232 A1 | 1/2018 | Mine et al. |
| 2018/0025492 A1 | 1/2018 | Honjo et al. |
| 2019/0244352 A1 | 8/2019 | Honjo et al. |
| 2019/0310681 A1 | 10/2019 | Shainwald et al. |
| 2019/0357874 A1 | 11/2019 | Yoshiara et al. |
| 2019/0378314 A1 | 12/2019 | Umezawa et al. |
| 2021/0315543 A1 | 10/2021 | Honjo et al. |
| 2021/0407084 A1 | 12/2021 | Honjo et al. |

FOREIGN PATENT DOCUMENTS

| | | |
|---|---|---|
| CN | 106560828 A | 4/2017 |
| CN | 110507356 A | 11/2019 |
| JP | 11-299785 A | 11/1999 |
| JP | 2000-342586 A | 12/2000 |
| JP | 2001-204729 A | 7/2001 |
| JP | 2003-126087 A | 5/2003 |
| JP | 2004-329742 A | 11/2004 |
| JP | 2006-014928 A | 1/2006 |
| JP | 2007-029248 A | 2/2007 |
| JP | 2007-260188 A | 10/2007 |
| JP | 2009-022307 A | 2/2009 |
| JP | 2011-072374 A | 4/2011 |
| JP | 2011-182983 A | 8/2011 |
| JP | 2012-115383 A | 6/2012 |
| JP | 2014-000260 A | 1/2014 |
| JP | 2014-012129 A | 1/2014 |
| JP | 2014-158698 A | 9/2014 |
| JP | 2015-131097 A | 7/2015 |
| JP | 2015-171425 A | 10/2015 |
| JP | 2016-534774 A | 11/2016 |
| JP | 2017-093913 A | 6/2017 |
| JP | 2017-104526 A | 6/2017 |
| JP | 2018-015155 A | 2/2018 |
| JP | 2018-020107 A | 2/2018 |
| JP | 2018-57695 A | 4/2018 |
| JP | 2018-079070 A | 5/2018 |
| JP | 2018-089822 A | 6/2018 |
| JP | 2018-108362 A | 7/2018 |
| JP | 2019-118820 A | 7/2019 |
| JP | 2019-181189 A | 10/2019 |
| JP | 2019-202144 A | 11/2019 |
| WO | WO 2011/114830 A1 | 9/2011 |

OTHER PUBLICATIONS

Combined Chinese Office Action and Search Report issued on Jul. 6, 2023 in Chinese Patent Application No. 202180003442.X, 7 pages.

Combined Chinese Office Action and Search Report issued Mar. 28, 2024 in Chinese Application 202180003442.X, (with English translation), 8 pages.

Office Action issued Mar. 19, 2025, in corresponding Japanese Patent Application No. 2021-088405 with English translation, 10 pages.

Office Action issued Jun. 29, 2024, in corresponding Chinese Patent Application No. 202180003442.X, 11 pages.

Office Action issued Jun. 18, 2025, in corresponding Japanese Patent Application No. 2021-088405, citing documents 15 and 16 therein, 3 pages.

* cited by examiner

FIG.7
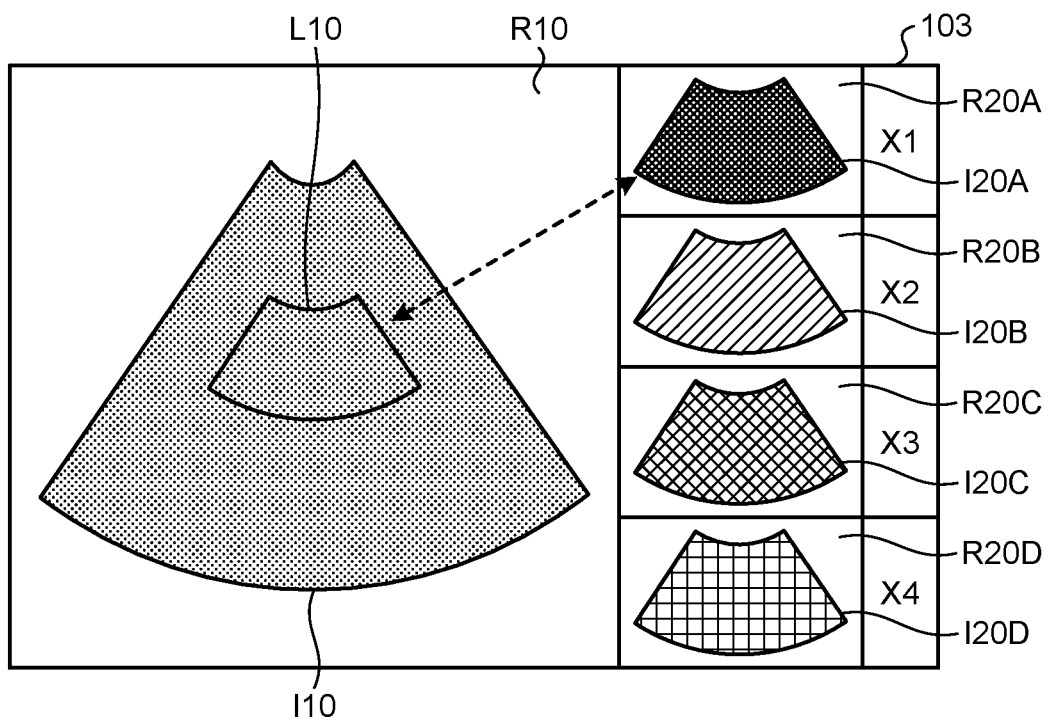
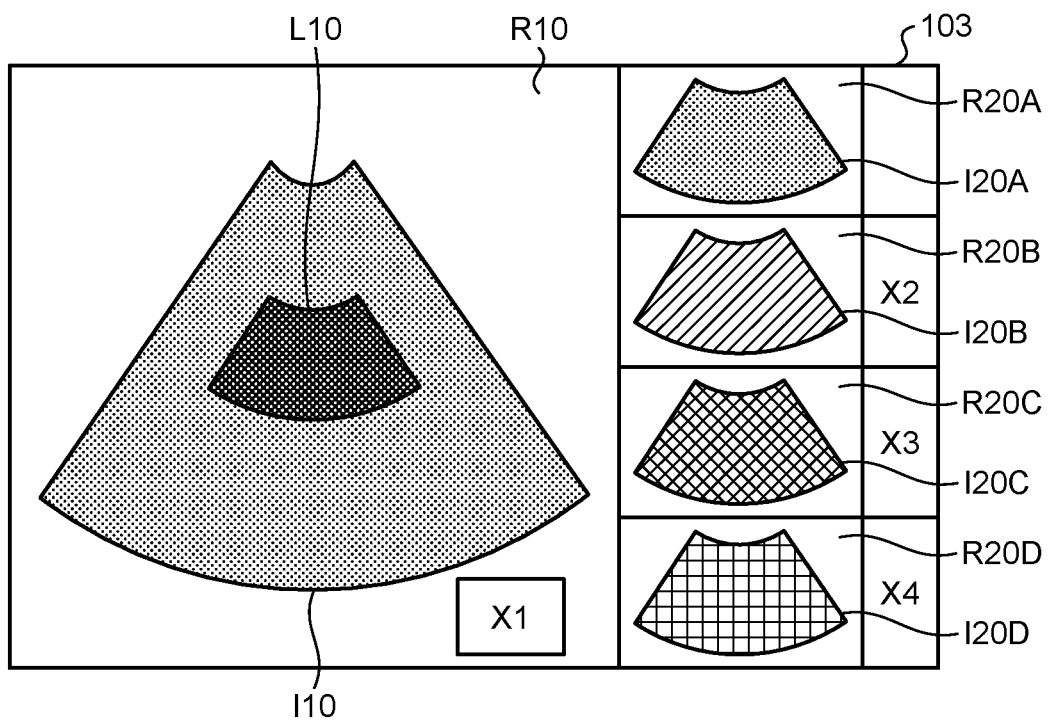

FIG.8
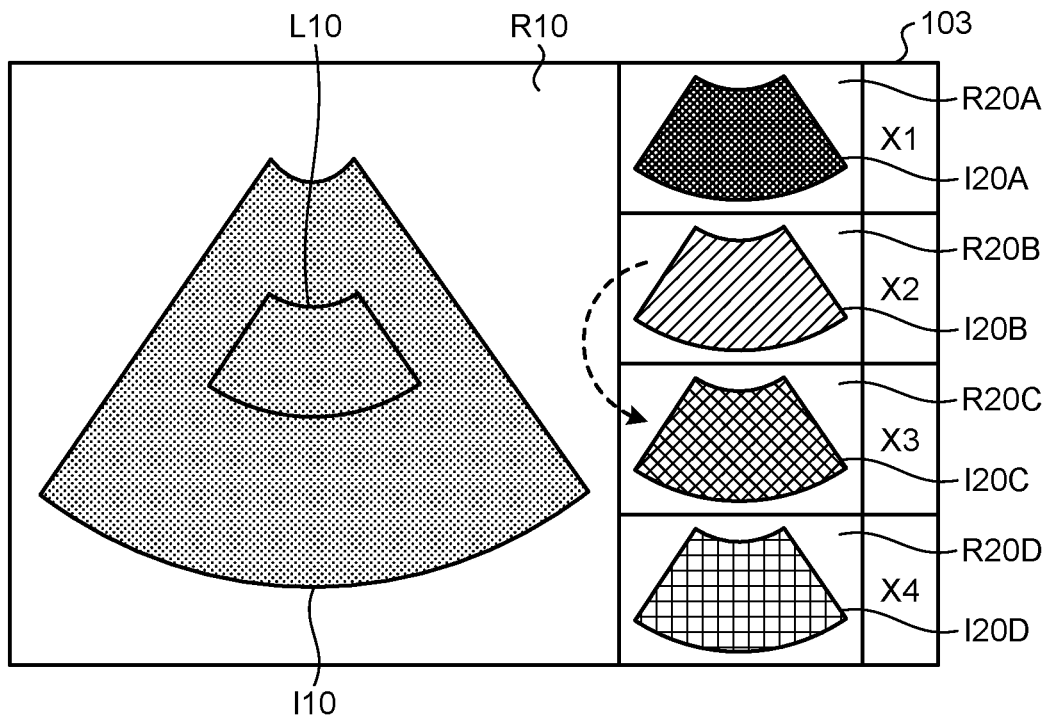
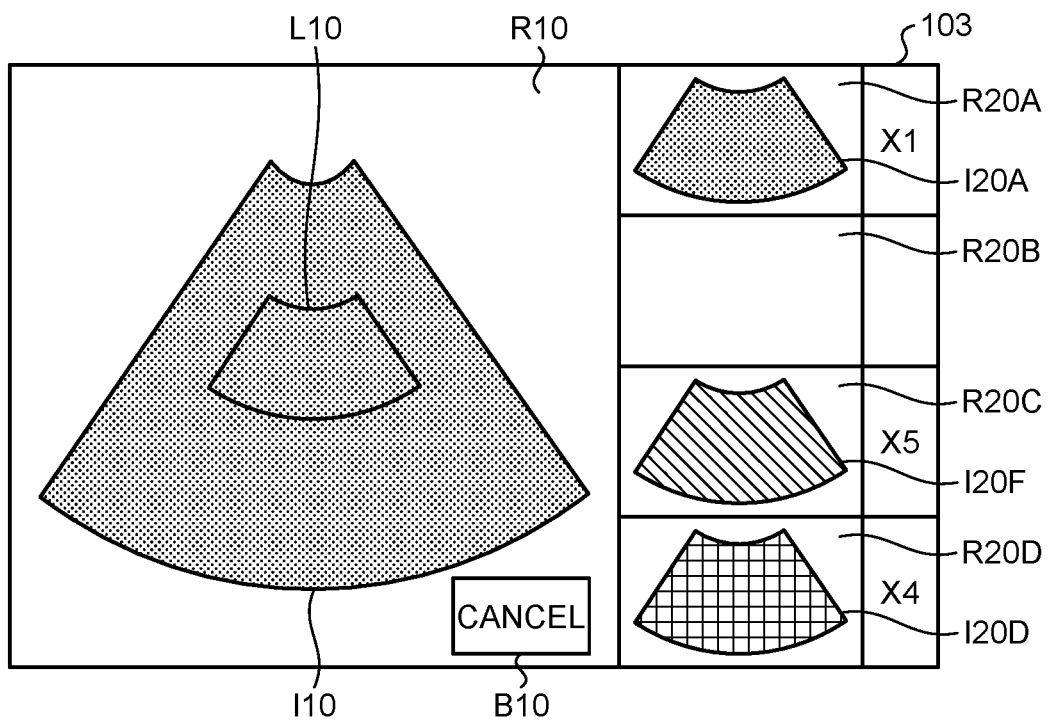

ULTRASOUND DIAGNOSIS APPARATUS AND IMAGE PROCESSING APPARATUS

CROSS-REFERENCE TO RELATED APPLICATIONS

This application is a continuation of PCT international application Ser. No. PCT/JP2021/019988, filed on May 26, 2021 which designates the United States, incorporated herein by reference, and which claims the benefit of priority from Japanese Patent Application No. 2020-091532, filed on May 26, 2020, the entire contents of which are incorporated herein by reference.

FIELD

Embodiments disclosed in this specification and the drawings relate to ultrasound diagnosis apparatuses and image processing apparatuses.

BACKGROUND

An ultrasound diagnosis apparatus is an apparatus that forms (captures) images of a state inside a living body by irradiating the interior of the living body with ultrasound generated by a piezoelectric transducer and receiving the ultrasound reflected in the living body. Ultrasound diagnosis apparatuses enable real time and non-invasive imaging that has thus been widely used in examination for various diseases.

B-mode images representing morphology of tissue in scanned cross-sections and analytical images resulting from analysis of bloodstream and various tissue characteristics are captured by ultrasound diagnosis apparatuses. For example, an analytical image is displayed in a state of being superimposed, at a corresponding position, on a B-mode image serving as a background.

BRIEF DESCRIPTION OF THE DRAWINGS

FIG. 7 is a diagram illustrating an example of a display screen according to a third modified example of the embodiment;

FIG. 8 is a diagram illustrating an example of a display screen according to a fourth modified example of the embodiment;

DETAILED DESCRIPTION

One of problems to be solved by embodiments disclosed in this specification and the drawings is to improve browsability of images. However, the problems to be solved by the embodiments disclosed in this specification and the drawings are not limited to the above problem. Any problems corresponding to effects provided by configurations disclosed by the embodiments described later may be regarded as alternative objects.

An ultrasound diagnosis apparatus includes processing circuitry. The processing circuitry causes plural images to be displayed in plural second display regions that have been arranged, the plural images being obtained by an ultrasound scan or ultrasound scans and corresponding to a region of interest in a morphology image displayed in a first display region.

An ultrasound diagnosis apparatus and an image processing apparatus according to embodiments will be described below by reference to the drawings. Embodiments are not limited to the following embodiments. Furthermore, description related to one of the embodiments is similarly applicable, in principle, to the other embodiments.

Embodiments

Figure 1:
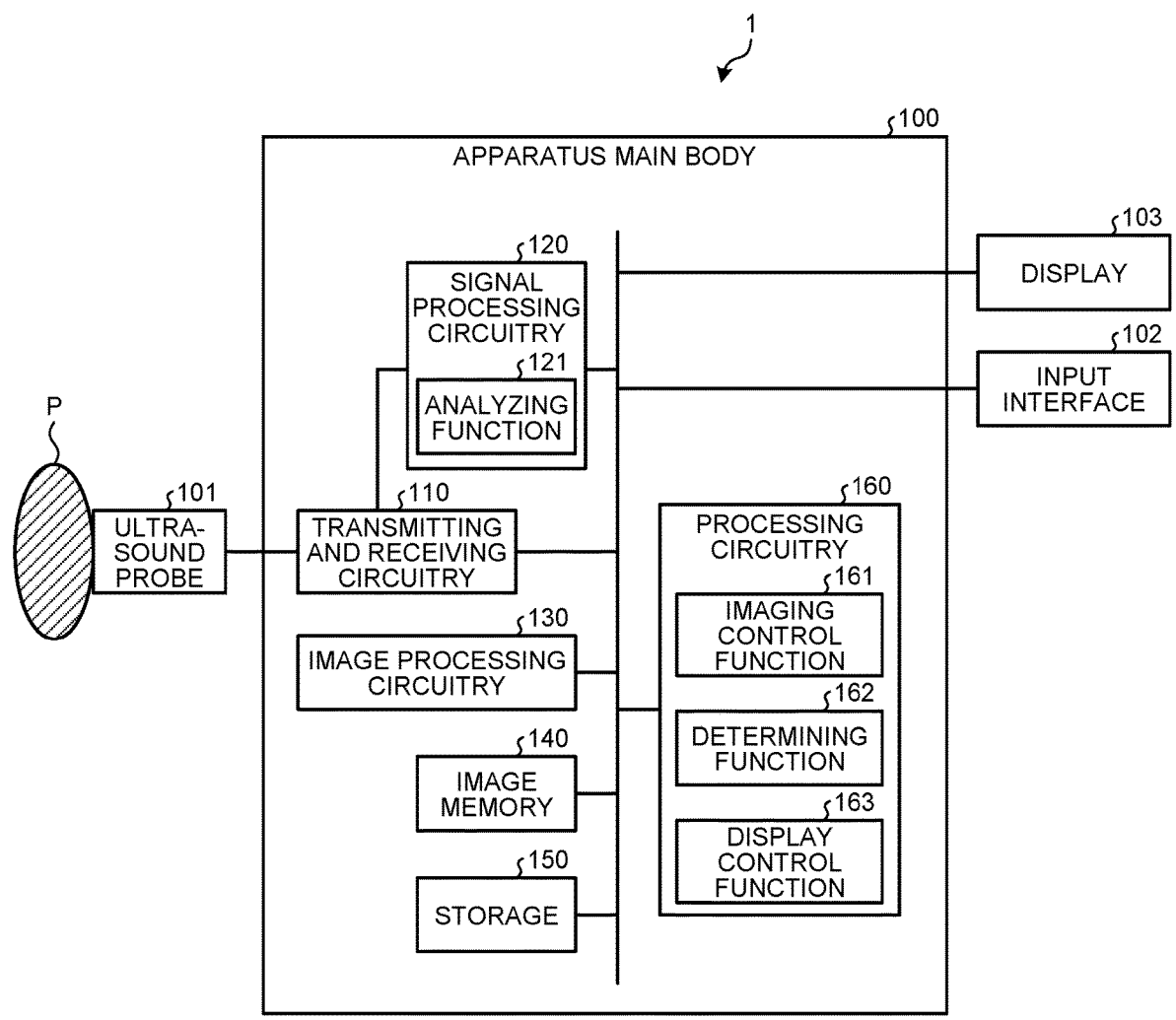
FIG. 1 is a block diagram illustrating an example of a configuration of an ultrasound diagnosis apparatus according to an embodiment.

FIG. 1 is a block diagram illustrating an example of a configuration of an ultrasound diagnosis apparatus 1 according to an embodiment. As illustrated in FIG. 1, the ultrasound diagnosis apparatus 1 according to the embodiment has an apparatus main body 100, an ultrasound probe 101, an input interface 102, and a display 103. The ultrasound probe 101, the input interface 102, and the display 103 are connected to the apparatus main body 100. A subject P is not included in the configuration of the ultrasound diagnosis apparatus 1.

The ultrasound probe 101 has plural transducers (for example, piezoelectric transducers) and these plural transducers generate ultrasound on the basis of driving signals supplied from transmitting and receiving circuitry 110 included in the apparatus main body 100 described later. Furthermore, the plural transducers included in the ultrasound probe 101 receive reflected waves from the subject P and convert the reflected waves into electric signals. The ultrasound probe 101 also has matching layers provided in the transducers, and a backing material that prevents propagation of ultrasound backward from the transducers, for example.

When ultrasound is transmitted from the ultrasound probe 101 to the subject P, the ultrasound transmitted is: successively reflected by a discontinuous surface of tissue in the body of the subject P, the discontinuous surface being where the acoustic impedance is discontinuous; and received as reflected wave signals (echo signals) by the plural transducers included in the ultrasound probe 101. Amplitude of the reflected wave signals received is dependent on the acoustic impedance difference at the discontinuous surface by which the ultrasound is reflected. If the transmitted ultrasound pulses are reflected by bloodstream or a surface of a cardiac wall that is moving, for example, frequency of the reflected wave signals is shifted dependently on velocity components of that moving body in relation to the direction in which the ultrasound is transmitted, due to the Doppler effect.

This embodiment is applicable to any of: a case where the ultrasound probe 101 illustrated in FIG. 1 is a one-dimensional ultrasound probe having the plural piezoelectric transducers arranged in one row; a case where the ultrasound probe 101 is a one-dimensional ultrasound probe having plural piezoelectric transducers that are arranged in one row and that are mechanically swung; and a case where the ultrasound probe 101 is a two-dimensional ultrasound probe having plural piezoelectric transducers two-dimensionally arranged in a grid-like pattern.

The input interface 102: has any of, for example, a mouse, a keyboard, buttons, panel switches, a touch command screen, foot switches, a trackball, and a joystick; receives various setting requests from an operator of the ultrasound diagnosis apparatus 1; and transfers the various setting requests received, to the apparatus main body 100.

The display 103 displays a graphical user interface (GUI) for an operator of the ultrasound diagnosis apparatus 1 to input the various setting requests using the input interface 102, and displays ultrasound image data generated at the apparatus main body 100, for example.

The apparatus main body 100 is an apparatus that generates ultrasound image data on the basis of reflected wave signals received by the ultrasound probe 101 and has, as illustrated in FIG. 1, the transmitting and receiving circuitry 110, signal processing circuitry 120, image processing circuitry 130, an image memory 140, a storage 150, and processing circuitry 160. The transmitting and receiving circuitry 110, the signal processing circuitry 120, the image processing circuitry 130, the image memory 140, the storage 150, and the processing circuitry 160 are connected to enable communication with one another. For example, at least a part of the transmitting and receiving circuitry 110 may be included in the ultrasound probe 101. Furthermore, for example, at least a part of the signal processing circuitry 120 may be included in the ultrasound probe 101. The apparatus main body 100 may be a tablet apparatus having a touch panel that is a main operating means of the tablet apparatus.

The transmitting and receiving circuitry 110 has a pulse generator, a transmission delay unit, and a pulser, for example, and supplies driving signals to the ultrasound probe 101. The pulse generator repeatedly generates a rate pulse for forming transmission ultrasound at a predetermined rate frequency. Furthermore, the transmission delay unit provides delay times respectively for the piezoelectric transducers to the respective rate pulses generated by the pulse generator, the delay times being required to converge the ultrasound generated by the ultrasound probe 101 into a beam form and to determine the transmission directivity. The pulser applies a driving signal (driving pulse) to the ultrasound probe 101 at a time that is based on a rate pulse. That is, by varying the delay times to be provided to the respective rate pulses, the transmission delay unit freely adjusts the transmission direction of ultrasound transmitted from surfaces of the piezoelectric transducers.

The transmitting and receiving circuitry 110 has a function of being capable of instantaneously changing the transmission frequency and the transmission driving voltage, for example, to execute a predetermined scan sequence on the basis of an instruction from the processing circuitry 160 described later. In particular, changing the transmission driving voltage is implemented by linear amplifier transmitting circuitry capable of changing the value instantaneously, or a system that electrically switches between plural power supply units.

Furthermore, the transmitting and receiving circuitry 110 has a preamplifier, an analog/digital (A/D) converter, a reception delay unit, and an adder, for example, and generates reflected wave data by performing various types of processing on the reflected wave signals received by the ultrasound probe 101. The preamplifier amplifies the reflected wave signals per channel. The A/D converter performs A/D conversion on the reflected wave signals that have been amplified. The reception delay unit provides a delay time required for determination of the reception directivity. The adder generates reflected wave data by performing addition processing on reflected wave signals processed by the reception delay unit. The addition processing by the adder enhances reflected components from a direction corresponding to the reception directivity of the reflected wave signals and overall beams for ultrasound transmission and reception are formed on the basis of the reception directivity and transmission directivity.

When a two-dimensional region of the subject P is to be scanned, the transmitting and receiving circuitry 110 causes an ultrasound beam to be transmitted two-dimensionally from the ultrasound probe 101. The transmitting and receiving circuitry 110 then generates two-dimensional reflected wave data from reflected wave signals received by the ultrasound probe 101. Furthermore, when a three-dimensional region of the subject P is to be scanned, the transmitting and receiving circuitry 110 causes an ultrasound beam to be transmitted three-dimensionally from the ultrasound probe 101. The transmitting and receiving circuitry 110 then generates three-dimensional reflected wave data from reflected wave signals received by the ultrasound probe 101.

The signal processing circuitry 120 generates data (B-mode data) in which the signal intensity of each sample point is represented by brightness, by performing logarithmic amplification and envelope detection processing, for example, on reflected wave data received from the transmitting and receiving circuitry 110. The B-mode data generated by the signal processing circuitry 120 are output to the image processing circuitry 130.

Furthermore, the signal processing circuitry 120 generates data (Doppler data) having movement information that is based on the Doppler effect of the moving body and that has been extracted at sample points in the scanned region, from reflected wave data received from the transmitting and receiving circuitry 110, for example. Specifically, the signal processing circuitry 120 performs frequency analysis on velocity information from the reflected wave data, extracts bloodstream, tissue, and contrast agent echo components due to the Doppler effect, and generates data (Doppler data) having moving body information, such as mean velocity, dispersion, and power, extracted for multiple points. The moving body herein is, for example, the bloodstream, tissue of the cardiac wall, or the contrast agent. The movement information (bloodstream information) obtained by the signal processing circuitry 120 is transmitted to the image processing circuitry 130 and displayed in color on the display 103 as a mean velocity image, a dispersion image, a power image, or an image having a combination of any of the mean velocity image, dispersion image, and power image.

Furthermore, the signal processing circuitry 120 executes an analyzing function 121, as illustrated in FIG. 1. A processing function executed by the analyzing function 121 that is a component of the signal processing circuitry 120 illustrated in FIG. 1 has been recorded in a storage device (for example, the storage 150) of the ultrasound diagnosis apparatus 1 in the form of a program executable by a computer, for example. The signal processing circuitry 120 is a processor that implements functions corresponding to programs by reading and executing the programs from the storage device. In other words, the signal processing circuitry 120 that has read the programs has functions illustrated inside the signal processing circuitry 120 in FIG. 1. The processing function executed by the analyzing function 121 will be described later.

The image processing circuitry 130 generates ultrasound image data from data generated by the signal processing circuitry 120. The image processing circuitry 130 generates B-mode image data having intensities of reflected waves from B-mode image data generated by the signal processing circuitry 120, the intensities being represented by brightness. Furthermore, the image processing circuitry 130 generates Doppler image data representing moving body information from Doppler data generated by the signal processing circuitry 120. The Doppler image data are velocity image data, dispersion image data, power image data, or image data having a combination of any of the velocity image data, dispersion image data, and power image data.

Typically, the image processing circuitry 130 generates ultrasound image data for display by converting (scan-converting) scan line signal strings from ultrasound scanning, into scan line signal strings having a video format typical of television, for example. Specifically, the image processing circuitry 130 generates ultrasound image data for display, by coordinate transformation according to the ultrasound scan mode of the ultrasound probe 101. Furthermore, the image processing circuitry 130 performs various types of image processing other than the scan-converting, the various types of image processing including, for example, image processing (smoothing processing) for regenerating a mean value image for brightness using plural image frames resulting from the scan-converting, and image processing (edge enhancement processing) using a differential filter in the image. The image processing circuitry 130 also combines the ultrasound image data with supplementary information (character information on various parameters, scales, and body marks).

That is, the B-mode data and Doppler data are ultrasound image data that have not been scan-converted yet, and data generated by the image processing circuitry 130 are the ultrasound image data for display resulting from the scan-converting. When the signal processing circuitry 120 generates three-dimensional data (three-dimensional B-mode data and three-dimensional Doppler data), the image processing circuitry 130 generates volume data by performing coordinate transformation according to the ultrasound scan mode of the ultrasound probe 101. The image processing circuitry 130 then generates two-dimensional image data for display, by performing various types of rendering processing on the volume data.

The image memory 140 is a memory that stores image data for display generated by the image processing circuitry 130. Furthermore, the image memory 140 may store data generated by the signal processing circuitry 120. B-mode data and Doppler data stored in the image memory 140 are, for example, able to be called by an operator after diagnosis, and formed into ultrasound image data for display via the image processing circuitry 130.

The storage 150 stores a control program for performing ultrasound transmission and reception, image processing, and display processing, and various data, such as diagnostic information (for example, patient IDs, and observations by doctors), diagnostic protocols, and various body marks. Furthermore, the storage 150 is used, as required, for storage of image data stored in the image memory 140, for example. Data stored in the storage 150 may also be transmitted to an external device via an interface not illustrated in the drawings.

The processing circuitry 160 controls the overall processing by the ultrasound diagnosis apparatus 1. Specifically, on the basis of various setting requests input by an operator via the input interface 102 and various control programs and various data read from the storage 150, the processing circuitry 160 controls processing by the transmitting and receiving circuitry 110, the signal processing circuitry 120, and the image processing circuitry 130. Furthermore, the processing circuitry 160 performs control such that ultrasound image data for display stored in the image memory 140 are displayed on the display 103.

Furthermore, as illustrated in FIG. 1, the processing circuitry 160 executes an imaging control function 161, a determining function 162, and a display control function 163. For example, processing functions respectively executed by the imaging control function 161, the determining function 162, and the display control function 163 that are components of the processing circuitry 160 illustrated in FIG. 1 have been recorded in the storage device (for example, the storage 150) of the ultrasound diagnosis apparatus 1 in the form of programs executable by a computer. The processing circuitry 160 is a processor that implements functions corresponding to the programs by reading and executing the programs from the storage device. In other words, the processing circuitry 160 that has read the programs has the functions illustrated inside the processing circuitry 160 in FIG. 1. The processing functions executed by the imaging control function 161, the determining function 162, and the display control function 163 will be described later.

The term, "processor (circuitry)", used in the above description means, for example: a central processing unit (CPU); a graphics processing unit (GPU); or a circuit, such as an application specific integrated circuit (ASIC) or a programmable logic device (for example, a simple programmable logic device (SPLD), a complex programmable logic device (CPLD), or a field programmable gate array (FPGA)). The processor implements its functions by reading and executing the programs stored in the storage 150. Instead of being stored in the storage 150, the programs may be directly incorporated in a circuit of the processor. In that case, by reading and executing the programs incorporated in the circuit, the processor implements the functions. Each of the processors according to the embodiment is not necessarily configured as a single circuit, and plural independent circuits may be combined together to be configured as a single processor to implement the functions. Furthermore, plural components in each drawing may also be integrated into a single processor to implement the functions.

The ultrasound diagnosis apparatus 1 according to the embodiment is an apparatus that enables analytical images to be captured, the analytical images being based on various parameters related to tissue characteristics, bloodstream, or quality. For example, various parameters related to tissue characteristics, bloodstream, or quality are calculated at the signal processing circuitry 120, for each sample point in a region of interest (ROI) corresponding to a scan range for obtainment of an analytical image. The image processing circuitry 130 generates various analytical images by assigning image values corresponding to various parameters at sample points to respective positions (sample points) in the ROI. The ultrasound diagnosis apparatus 1 displays the various analytical images generated.

Examples of an analytical image based on a parameter related to a tissue characteristic include an image representing elasticity (elasticity image), an image related to viscosity (viscosity image), and an image (attenuation image) representing attenuation of ultrasound (corresponding to the amount of fat). An elasticity image is generated by, for example: transmitting displacement generating ultrasound (push pulses) for generating shear waves to a subject; observing the shear waves generated through transmission and reception of ultrasound (tracking pulses) for displacement observation; thereby obtaining temporal change information on displacement due to the shear waves for each position in a region of interest; finding an arrival time of the shear waves at each position in the region of interest, on the basis of the temporal change information on displacement obtained; finding velocities of the shear waves on the basis of the arrival times found; and assigning a pixel value corresponding to the velocity found to each position in the region of interest. Any publicly known technique, such as a technique described in JP2014-000260A, for example, may be applied to the generation of elastic images and parameter calculation. Furthermore, a viscosity image is generated by, for example: transmitting deformation generating ultrasound (push pulses) for generating shear waves, to a subject; observing the shear waves generated through transmission and reception of ultrasound (tracking pulses) for displacement observation; thereby obtaining temporal change information on displacement due to the shear waves for each position in a region of interest; performing frequency analysis on the temporal change information on displacement obtained; generating a distribution representing a relation between shear velocity and frequency for each position in the region of interest; and assigning a value calculated on the basis of that relation, to each pixel. Any publicly known technique, such as a technique described in JP2017-104526A, for example, may be applied to the generation of images related to viscosity and parameter calculation, without being limited to viscosity values. Furthermore, an attenuation image is generated by, for example: obtaining processed reflected wave data by executing, on reflected wave data obtained by transmission and reception of ultrasound, processing for offsetting signal amplification parts due to various gains and processing for offsetting influence of the sound field; differentiating the processed reflected wave data obtained, along the direction (depth direction) in which the ultrasound is transmitted and received; thereby obtaining an attenuation index value for each position in a region of interest; and assigning the attenuation index values obtained to the respective positions in the region of interest. The attenuation image may be generated by using the reflected wave data that are the same as those of the B-mode image for the background. Any publicly known technique, such as a technique described in JP2017-093913A, for example, may be applied to the generation of attenuation images and parameter calculation.

Furthermore, examples of an analytical image based on a parameter related to bloodstream include medium to high velocity bloodstream images, low velocity bloodstream images, and various contrast-enhanced images. Any publicly known technique, such as a technique described in JP2000-342586A, for example, is applicable to the generation of medium to high velocity bloodstream images and parameter calculation. Furthermore, any publicly known technique, such as a technique described in JP2014-158698A, for example, is applicable to the generation of low velocity bloodstream images and parameter calculation. In addition, any publicly known technique is applicable to various contrast-enhanced images, such as, for example, an image obtained by adding up pixel values at respective positions in the time direction, an image obtained by holding the largest one of pixel values at respective positions in the time direction, an image representing arrival times of a contrast agent at respective positions, or an image representing the amount of movement, the moving velocity, or the moving direction of a contrast agent obtained by tracking the contrast agent between time phases (a technique described in JP2018-015155A).

Furthermore, examples of an analytical image (quality image) based on a parameter related to quality include an image representing a distribution of arrival times of shear waves, an image representing a distribution of dispersed values of arrival time, and an image representing a spatial or temporal variation of a parameter related to a tissue characteristic. Any publicly known technique, such as a technique described in JP2014-000260A, JP2015-131097A, or JP2018-020107A, for example, may be applied to the generation of quality images and parameter calculation.

Furthermore, the ultrasound diagnosis apparatus 1 may also be an apparatus that enables imaging of analytical images (temporal change images) based on a parameter related to temporal change in echo intensity. That is, the ultrasound diagnosis apparatus 1 is an apparatus that enables imaging of analytical images based on various parameters related to a tissue characteristic, bloodstream, quality, or temporal change in echo intensity.

Furthermore, examples of an analytical image (temporal change image) based on a parameter related to temporal change (fluctuation) in echo intensity include an image resulting from detection of spatial and temporal fluctuation after removal of any fluctuation component in the background, and an image representing temporal direction statistical values (such as dispersion) of similarity between image signals in medical images between two time phases. The temporal change in echo intensity is considered to be one of characteristic observations for hemangiomas. Any publicly known technique, such as a technique described in JP2018-089822A or JP2019-181189A, for example, may be applied to the generation of temporal change images and parameter calculation.

In other words, a first parameter is a parameter related to elasticity of tissue, viscosity of tissue, attenuation of ultrasound, quality of a second parameter, low velocity bloodstream, high velocity bloodstream, or temporal change in echo intensity. Furthermore, the second parameter is a parameter related to elasticity of tissue, viscosity of tissue, attenuation of ultrasound, quality of the second parameter, low velocity bloodstream, high velocity bloodstream, or temporal change in echo intensity. The first parameter and the second parameter are preferably different from each other.

An example of the configuration of the ultrasound diagnosis apparatus 1 according to the embodiment has been described above. The ultrasound diagnosis apparatus 1 according to the embodiment and having this configuration executes the following processing to improve browsability of images.

Figure 2:
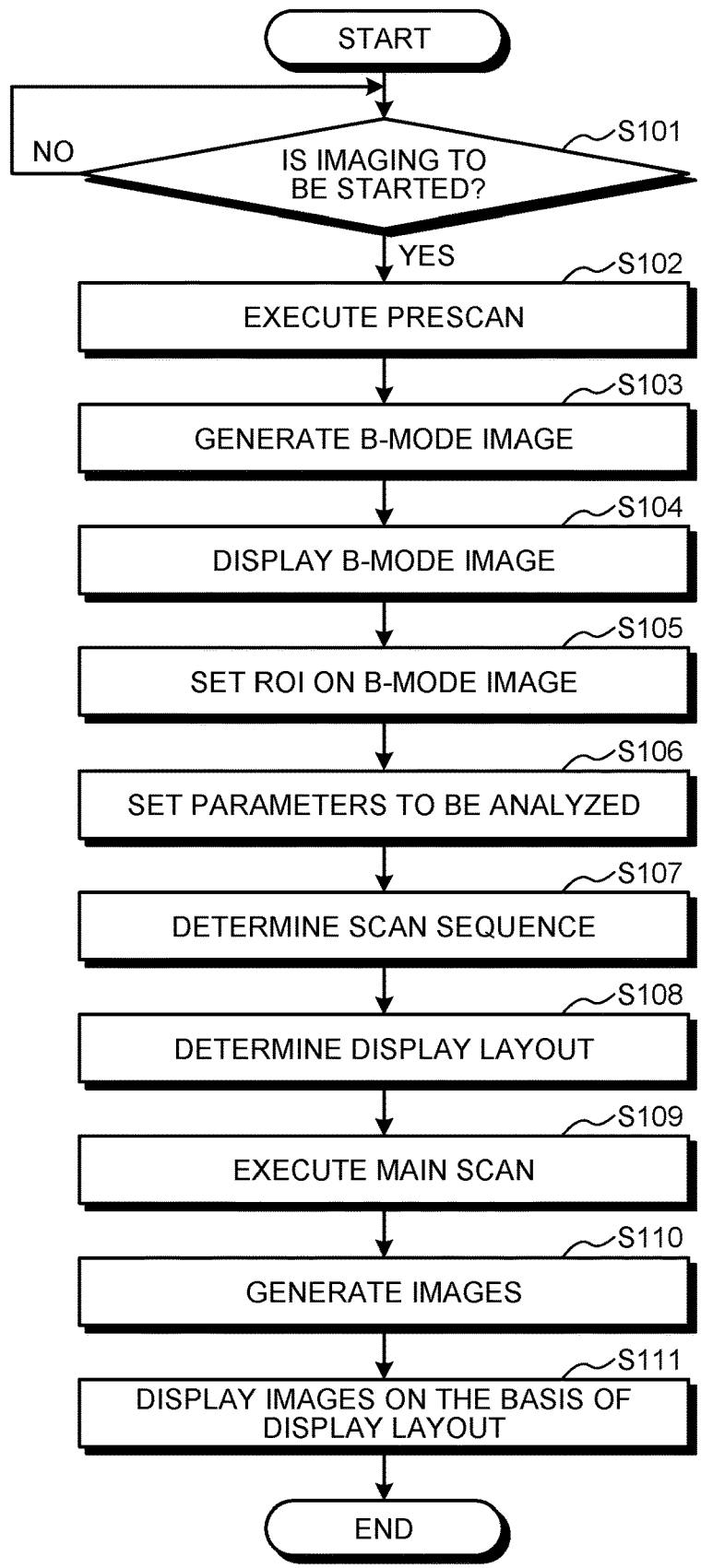
FIG. 2 is a flowchart illustrating a processing procedure by the ultrasound diagnosis apparatus according to the embodiment.

FIG. 2 is a flowchart illustrating a processing procedure by the ultrasound diagnosis apparatus 1 according to the embodiment. The processing procedure illustrated in FIG. 2 is started by an operator instructing start of imaging, for example.

As illustrated in FIG. 2, when an instruction to start imaging is received (Yes at Step S101), the processing circuitry 160 starts processing from Step S102. The processing procedure in FIG. 2 is in standby until the instruction to start imaging is received (No at Step S101).

Subsequently, the imaging control function 161 executes a prescan (Step S102). For example, the imaging control function 161 causes the transmitting and receiving circuitry 110 to execute, as the prescan, an ultrasound scan (B-mode scan) for generating a B-mode image serving as a background image. The transmitting and receiving circuitry 110 generates reflected wave data corresponding to a field of view (FOV) corresponding to a scan range by transmitting and receiving ultrasound to and from each scan line included in the FOV.

The image processing circuitry 130 then generates a B-mode image (Step S103). For example, the signal processing circuitry 120 generates B-mode data corresponding to the FOV, from the reflected wave data generated by the transmitting and receiving circuitry 110 and corresponding to the FOV. The image processing circuitry 130 then generates a B-mode image corresponding to the FOV, from the B-mode data corresponding to the FOV. The B-mode image is an example of a "morphology image". For example, the morphology image is an image representing morphology of tissue in the living body.

The display control function 163 then causes the B-mode image to be displayed (Step S104). For example, the display control function 163 causes the display 103 to display the B-mode image generated by the image processing circuitry 130 and corresponding to the FOV.

The displaying of the B-mode image is executed in real time until a main scan described later is executed. That is, the processing from Step S102 to Step S104 is repeatedly executed until the processing at Step S109 is executed.

The analyzing function 121 then sets an ROI on the B-mode image (Step S105). For example, the analyzing function 121 causes a frame line indicating position and size of the ROI to be displayed on the B-mode image, according to a request by an operator. The operator performs an operation to change (adjust) position and size (depth direction and lateral direction) of the frame line displayed on the B-mode image to a desired position and a desired size. When the operator has performed an operation to confirm the position and size of the frame line, the analyzing function 121 sets the frame line having the confirmed position and size as the ROI. In this embodiment, the ROI has a shape corresponding to the shape of the B-mode image. For example, if the B-mode image is quadrangular (square, rectangular, trapezoidal, or parallelogrammic), the ROI is quadrangular. Furthermore, if the B-mode image has a fan shape (including an annular fan shape), the ROI is fan-shaped.

Furthermore, the analyzing function 121 sets parameters to be analyzed (Step S106). For example, an operator performs an operation to select, as the parameters to be analyzed, four types of parameters, elasticity, viscosity, quality, and attenuation. In response to this operation, the analyzing function 121 sets, as the parameters to be analyzed, the four types of parameters, elasticity, viscosity, quality, and attenuation. That is, the analyzing function 121 is an example of a "setting unit" that sets a region of interest for the morphology image and determines parameters to be analyzed, in the region of interest.

The imaging control function 161 then determines a scan sequence (Step S107). For example, the imaging control function 161 determines a scan sequence for executing an ultrasound scan for obtaining a B-mode image, an ultrasound scan for obtaining an elasticity image, a viscosity image, and a quality image, and an ultrasound scan for obtaining an attenuation image, in order. The imaging control function 161 transmits the scan sequence determined, to the transmitting and receiving circuitry 110.

Because the elasticity image, viscosity image, and quality image are able to be generated on the basis of common reflected wave data, they are preferably generated by the same ultrasound scan. The imaging control function 161 is an example of a "scan control unit".

The determining function 162 then determines a display layout (Step S108). For example, the determining function 162 determines a display arrangement for a first display region where the B-mode image is to be displayed and plural second display regions where plural analytical images are to be displayed, on the basis of the number of analytical images corresponding to the ROI. The determining function 162 is an example of a "determining unit". Furthermore, the display layout is an example of a "display arrangement".

For example, the determining function 162 determines the arrangement for the plural second display regions, on the basis of the number of analytical images. Specifically, when the number of analytical images is "4" or less, the determining function 162 determines a "single vertical line form" as the arrangement of the plural second display regions. Correspondence between the numbers of analytical images and arrangements have been set beforehand and stored in any storage device (for example, the storage 150).

The processing by the determining function 162 is not limited to the processing described above. For example, the display layout determined by the determining function 162 is not limited to the "single vertical line form". Other display layouts will be described later.

Furthermore, the determining function 162 may determine a display layout on the basis of the type of an analytical image, instead of the number of analytical images. For example, when the plural analytical images include an "elasticity image", the determining function 162 determines the arrangement of the plural second display regions to be the "single vertical line form". Correspondence between types of analytical images and arrangements have been set beforehand and stored in any storage device (for example, the storage 150).

Furthermore, the determining function 162 may determine a display layout on the basis of the position, size, or shape of the ROI. For example, on the basis of the height and width of a frame line L10, the determining function 162 may adjust the height and width of each of the plural second display regions or change the display layout to another display layout.

The transmitting and receiving circuitry 110 then executes a main scan (Step S109). For example, the transmitting and receiving circuitry 110 executes the scan sequence determined by the imaging control function 161. That is, the transmitting and receiving circuitry 110 executes a series of ultrasound scans including the ultrasound scan for obtaining a B-mode image, the ultrasound scan for obtaining an elasticity image, a viscosity image, and a quality image, and the ultrasound scan for obtaining an attenuation image. The transmitting and receiving circuitry 110 is an example of a "scan unit" or "scan circuitry".

The processing by the transmitting and receiving circuitry 110 is not limited to the processing described above. For example, the series of ultrasound scans executed by the transmitting and receiving circuitry 110 may include or not include an ultrasound scan for collecting plural types of analytical images by the same scan, the plural types of analytical images being, for example, an elasticity image, a viscosity image, and a quality image. That is, the transmitting and receiving circuitry 110 may execute a series of ultrasound scans including an ultrasound scan for obtaining the morphology image and an ultrasound scan for obtaining a first image and a second image. Furthermore, the transmitting and receiving circuitry 110 may execute a series of ultrasound scans including an ultrasound scan for obtaining the morphology image, an ultrasound scan for obtaining a first image, and an ultrasound scan for obtaining a second image.

The "series of ultrasound scans" includes plural types of ultrasound scans for obtaining plural types of parameters and is executed as a single scan sequence. For example, in a case where a series of ultrasound scans including an ultrasound scan for obtaining a B-mode image, an ultrasound scan for obtaining an elasticity image, and an ultrasound scan for obtaining an attenuation image is executed, these three ultrasound scans are executed as a single scan sequence. When this scan sequence is started, an operator holds (fixes) the ultrasound probe 101 that has been brought into contact with the subject P so as to not move the ultrasound probe 101 until the three ultrasound scans included in the scan sequence are completed. Positional information on the scanned range (sample points) is thus kept consistent among the B-mode image, elasticity image, and attenuation image obtained by the series of ultrasound scans.

The image processing circuitry 130 then generates images (analytical images) (Step S110). For example, the signal processing circuitry 120 generates B-mode data corresponding to the FOV, from the reflected wave data generated by the transmitting and receiving circuitry 110 and corresponding to the FOV. The image processing circuitry 130 then generates a B-mode image corresponding to the FOV, from the B-mode data corresponding to the FOV.

Furthermore, for example, the analyzing function 121 calculates, for each sample point in the ROI, the four types of parameters (elasticity, viscosity, quality, and attenuation) set as targets to be analyzed. The image processing circuitry 130 then generates various analytical images (an elasticity image, a viscosity image, a quality image, and an attenuation image) by assigning image values corresponding to the various parameters at the respective sample points to respective positions in the ROI.

The display control function 163 then displays these images (analytical images) on the basis of a display layout (Step S111). For example, the display control function 163 causes plural images obtained by an ultrasound scan and corresponding to the region of interest in the morphology image displayed in the first display region, to be displayed in the plural second display regions that have been arranged. The display control function 163 is an example of a "display control unit".

Figure 3:
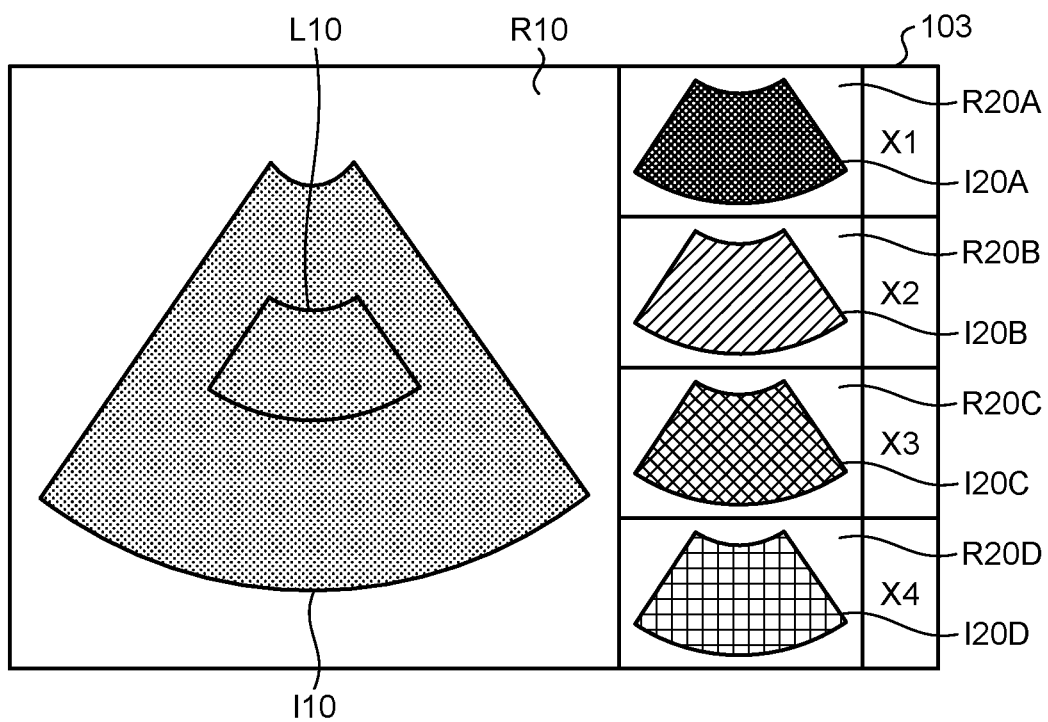
FIG. 3 is a diagram for explanation of processing by a display control function according to the embodiment.

FIG. 3 is a diagram for explanation of processing by the display control function 163 according to the embodiment. FIG. 3 illustrates an example of a display screen displayed on the display 103.

As illustrated in FIG. 3, the display control function 163 causes a B-mode image I10 to be displayed in a first display region R10. Furthermore, the display control function 163 causes the frame line L10 indicating the position and size of the ROI, to be displayed on the B-mode image I10.

Furthermore, the display control function 163 causes four second display regions R20A, R20B, R20C, and R20D to be displayed in the "single vertical line form" on the right of the first display region R10. The display control function 163 causes four analytical images I20A, I20B, I20C, and I20D to be respectively displayed in the four second display regions R20A, R20B, R20C, and R20D. For example, the analytical image I20A corresponds to an elasticity image. The analytical image I20B corresponds to a viscosity image. The analytical image I20C corresponds to a quality image. The analytical image I20D corresponds to an attenuation image.

Furthermore, the display control function 163 causes four values X1, X2, X3, and X4 to be respectively displayed inside or near the four second display regions R20A, R20B, R20C, and R20D. The value X1 is, for example, a representative value of the elasticity image. The value X2 is a representative value of the viscosity image. The value X3 is a representative value of the quality image. The value X4 is a representative value of the attenuation image. The representative value may be a value of the parameter of a representative point in the ROI, or may be a publicly known statistical value, such as the mean value, the median, the standard deviation, the maximum value, or the minimum value. The display control function 163 may display character strings indicating the types of the analytical images displayed, inside or near the four second display regions R20A, R20B, R20C, and R20D. Furthermore, the display control function 163 may display correspondence maps, such as color bars indicating relations between pixel values and values of the parameters of the displayed analytical images, inside or near the four second display regions R20A, R20B, R20C, and R20D.

The processing by the display control function 163 is not limited to that described by reference to FIG. 3. For example, the display layout displayed by the display control function 163 may have the single vertical line form in which the plural second display regions are arranged in the vertical direction to the left of the display screen. Furthermore, the display layout is not limited to the "single vertical line form". Other display layouts will be described later.

Furthermore, the display control function 163 may display an analytical image that has been combined with the morphology image (background image), in each of the second display regions. However, instead of the whole region of the morphology image, an image limited to a region smaller than the field of view of the morphology image is preferably displayed in each of the second display regions. That is, each analytical image is an image corresponding to the ROI, or an image limited to a region including the ROI and smaller than the field of view of the B-mode image.

Furthermore, the analytical images displayed in the second display regions are not necessarily the four analytical images, the elasticity image, viscosity image, quality image, and attenuation image. The display control function 163 may display at least two of the analytical images described above.

Furthermore, the analytical images to be displayed in the plural second display regions are not necessarily displayed in the order of the elasticity image, viscosity image, quality image, and attenuation image. For example, on the basis of "degrees of priority of parameters", the display control function 163 may determine the display order for the analytical images displayed in the plural second display regions. The "degrees of priority of parameters" may be preset, or any order specified by an operator may be adopted. The specification of the order by the operator may be received as an individual operation, or the order selected by an operator in the processing (Step S106) for setting the parameters to be analyzed may be adopted. That is, on the basis of the degrees of priority of the first parameter and the second parameter, the display control function 163 determines the display order for the plural images displayed in the second display regions. The first parameter and the second parameter are parameters different from each other.

Furthermore, in FIG. 3, the four second display regions R20A, R20B, R20C, and R20D are arranged continuously (arranged adjacent to each other), but the embodiment is not limited to this arrangement. For example, the plural second display regions may be arranged at intervals each narrower than a width of each of the second display regions, the width being along their arrangement direction. That is, the plural second display regions are arranged continuously or at intervals narrower than the widths of the second display regions, the widths being along the arrangement direction.

Furthermore, FIG. 3 illustrates the case where the orientation of the frame line L10 of the ROI and the orientation of each analytical image are the same, but the embodiment is not limited to this case. For example, even if the orientation of the frame line L10 of the ROI has been steered by an angle, the display control function 163 may display each analytical image such that the depth direction of the scan line in the center of the analytical image coincides approximately with the vertical direction on the screen. "Coinciding approximately with" herein is not limited to mean "coinciding" exactly and is intended to allow any difference within a range not significantly affecting the browsability.

Furthermore, the values X1, X2, X3, and X4 for the analytical images are not necessarily displayed on the right of the respective second display regions. For example, the display control function 163 may display a value inside or around one of the plural second display regions, the value having been obtained by measurement using the corresponding image.

Furthermore, the scale of enlargement for an image displayed in the first display region and the scale of enlargement for each image displayed in the second display regions are preferably the same, but are not necessarily the same.

Furthermore, the plural second display regions may be included in a divided region forming, like the first display region, at least a part of the display screen, or may be included in a window to be superimposed on the first display region.

Furthermore, the plural second display regions may be changeable in position and size according to an operation by an operator.

There are preferable combinations of plural images to be concurrently displayed in the second display regions. For example, an elasticity image and a viscosity image are preferably displayed concurrently. That is, the first parameter is a parameter related to elasticity of tissue and the second parameter is a parameter related to viscosity of the tissue.

Furthermore, an elasticity image is preferably displayed concurrently with a quality image representing quality of elasticity in that elasticity image. That is, the first parameter is a parameter related to elasticity of tissue and the second parameter is a parameter related to quality of the first parameter.

Furthermore, an attenuation image is preferably displayed concurrently with an elasticity image. That is, the first parameter is a parameter related to elasticity of tissue and the second parameter is a parameter related to attenuation of ultrasound.

Furthermore, a temporal change image is preferably displayed concurrently with an elasticity image. That is, the first parameter is a parameter related to temporal change in echo intensity and the second parameter is a parameter related to elasticity of tissue.

Description will now be made by reference to FIG. 2 again. The processing circuitry 160 ends the processing procedure in FIG. 2 when the images have been displayed.

The above described processing procedure in FIG. 2 is just an example, and the embodiment is not limited to the above described example. For example, the processing procedure in FIG. 2 is not necessarily executed in the above described order. The processing procedure in FIG. 2 may be modified freely so long as the modified processing procedure does not cause any inconsistency.

For example, the process (Step S106) of setting parameters to be analyzed and the process (Step S107) of determining a scan sequence may be executed together as a single process or may be executed before the prescan (Step S102).

Furthermore, the process (Step S108) of determining a display layout may be executed at any time after the process (Step S106) of setting parameters to be analyzed if the display layout is not dependent on the position or size of the ROI.

Furthermore, the above described processing procedure in FIG. 2 corresponds to the case where each analytical image is generated and displayed by real time processing of data collected by a main scan (ultrasound scan), but the embodiment is not limited to this case. For example, the process of generating and displaying each analytical image may be executed as a post-process.

As described above, the display control function 163 in the ultrasound diagnosis apparatus 1 according to the embodiment displays plural images in plural second display regions that have been arranged, the plural images being obtained by an ultrasound scan and corresponding to a region of interest in the morphology image displayed in a first display region. The ultrasound diagnosis apparatus 1 thereby improves browsability of the images.

Figure 4:
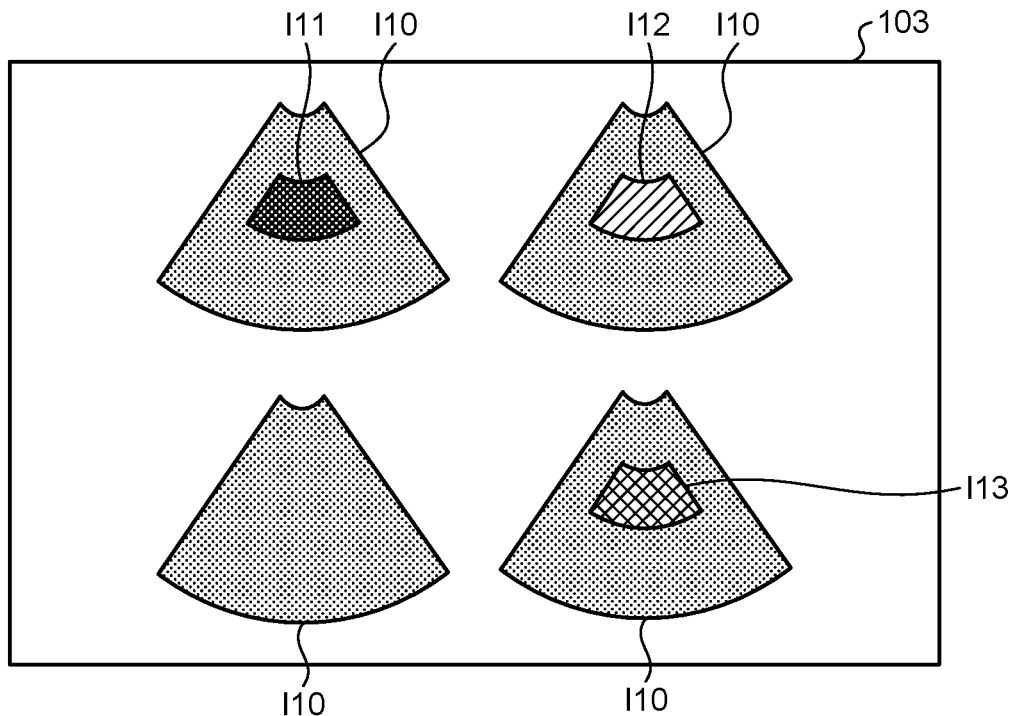
FIG. 4 is a diagram illustrating an example of a display screen according to a comparative example.

Effects by the ultrasound diagnosis apparatus 1 according to the embodiment will now be described using a comparative example. FIG. 4 is a diagram illustrating an example of a display screen according to the comparative example. FIG. 4 is an example of a display screen to which the above described processing at the ultrasound diagnosis apparatus 1 is not applied.

As illustrated in FIG. 4, in the case where the above described processing at the ultrasound diagnosis apparatus 1 is not used, plural analytical images I11, I12, and I13 may be displayed, for example, by being superimposed on individual B-mode images I10. In this case, the B-mode images I10 are displayed at four positions, the analytical image I11 is superimposed on the B-mode image I10 at the upper left, the analytical image I12 is superimposed on the B-mode image I10 at the upper right, and the analytical image I13 is superimposed on the B-mode image I10 at the bottom right.

However, on the display screen illustrated in FIG. 4, the analytical images I11, I12, and I13 are largely separated from one another and when an analyst (an operator) tries to refer to all of the analytical images I11, I12, and I13, the analyst's line of sight would thus need to move over a long distance and browsability may thus be unsatisfactory for the analyst. Furthermore, a large proportion of the whole display region is occupied by information other than the analytical image (the portion other than the ROI in the B-mode image, or a blank region), and thus the analytical image is displayed relatively (or absolutely depending on the screen size) small and the browsability may thus be unsatisfactory.

In contrast, the ultrasound diagnosis apparatus 1 according to the embodiment displays analytical images as exemplified by FIG. 3. The analytical images are brought close to each other as compared to those in the display screen in the comparative example, the distance of movement of the line of sight of an analyst is thus able to be decreased, and browsability for the analyst is thus able to be improved. Furthermore, as compared to the display screen in the comparative example, a smaller proportion of the whole display region is occupied by information other than the analytical images, and thus the analytical images are able to be displayed relatively large and the browsability is able to be improved. As a result, the ultrasound diagnosis apparatus 1 enables improvement in efficiency of analysis by the analyst, for example.

Therefore, in this embodiment, the first parameter may be a parameter related to elasticity of tissue and the second parameter may be a parameter related to viscosity of the tissue. Furthermore, the first parameter may be a parameter related to elasticity of tissue and the second parameter may be a parameter related to quality of the first parameter. Furthermore, the first parameter may be a parameter related to elasticity of tissue and the second parameter may be a parameter related to attenuation of ultrasound.

First Modified Example

In the above described embodiment, the display layout has the "single vertical line form", but the embodiment is not limited to this display layout. For example, the display layout may have an "L-shaped form".

Figure 5:
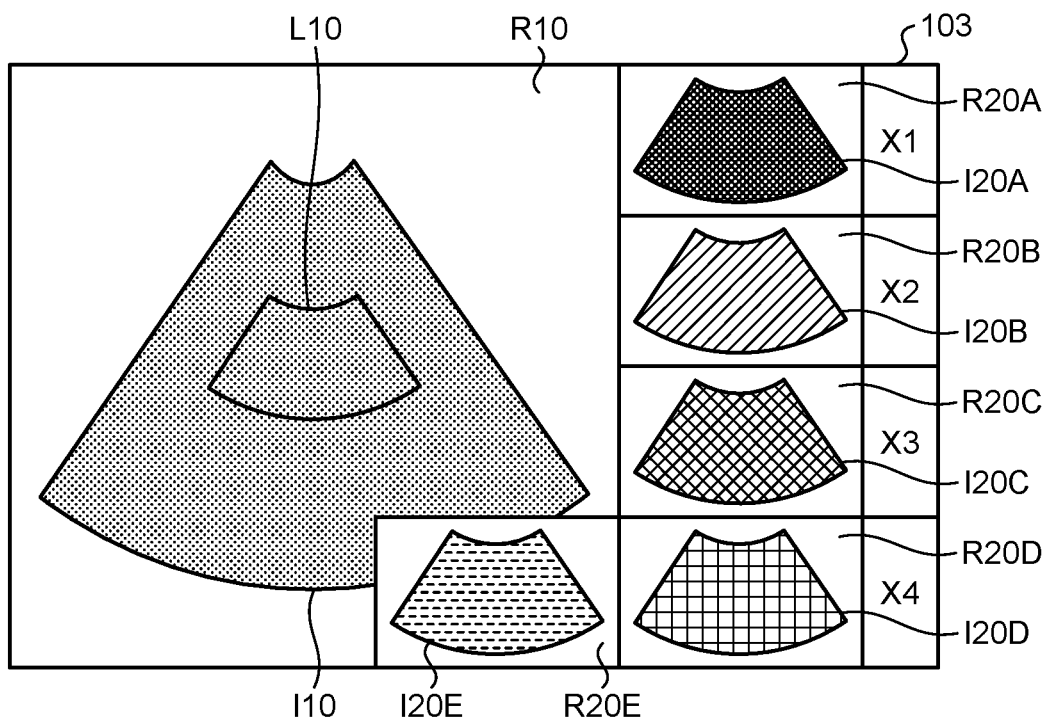
FIG. 5 is a diagram illustrating an example of a display screen according to a first modified example of the embodiment.

FIG. 5 is a diagram illustrating an example of a display screen according to a first modified example of the embodiment. As illustrated in FIG. 5, when the number of analytical images is "5", the determining function 162 determines the display arrangement of the plural second display regions to be the "L-shaped form". The display control function 163 then causes the plural second display regions to be displayed in the "L-shaped form" determined by the determining function 162.

In the example illustrated in FIG. 5, the display control function 163 arranges five second display regions R20A, R20B, R20C, R20D, and R20E in the L-shaped form (an L-shaped form that has been flipped horizontally, to be more exact). Furthermore, the display control function 163 causes an analytical image I20A to be displayed in the second display region R20A, an analytical image I20B to be displayed in the second display region R20B, an analytical image I20C to be displayed in the second display region R20C, an analytical image I20D to be displayed in the second display region R20D, and an analytical image I20E to be displayed in the second display region R20E.

The display layout for the plural second display regions is not limited to the above described "single vertical line form" or "L-shaped form". For example, the display layout for the plural second display regions may be a "double vertical line form", a "single horizontal line form", a "double horizontal line form", or a "matrix form". The "double vertical line form" is a form where the plural second display regions are lined up to both the left and the right of a display screen. The "single horizontal line form" is a form where the plural second display regions are lined up at the top or bottom of a display screen. The "double horizontal line form" is a form where the plural second display regions are lined up at both the top and bottom of a display screen. The "matrix form" is a form where the plural second display regions are lined up such that an n×m matrix is formed (where n and m are both integers of 2 or larger) at any position (preferably at any one of the top, bottom, left, and right) of a display screen. That is, the determining function 162 may determine the display arrangement to be any one of the single vertical line form, the double vertical line form, the single horizontal line form, the double horizontal line form, the matrix form, and the L-shaped form. Furthermore, the display control function 163 may cause the plural second display regions to be displayed in the display arrangement determined by the determining function 162.

Second Modified Example

The above described embodiment is also applicable to a case where a measurement region (an ROI for measurement) is set separately from the ROI (ROI for display) described above.

Figure 6:
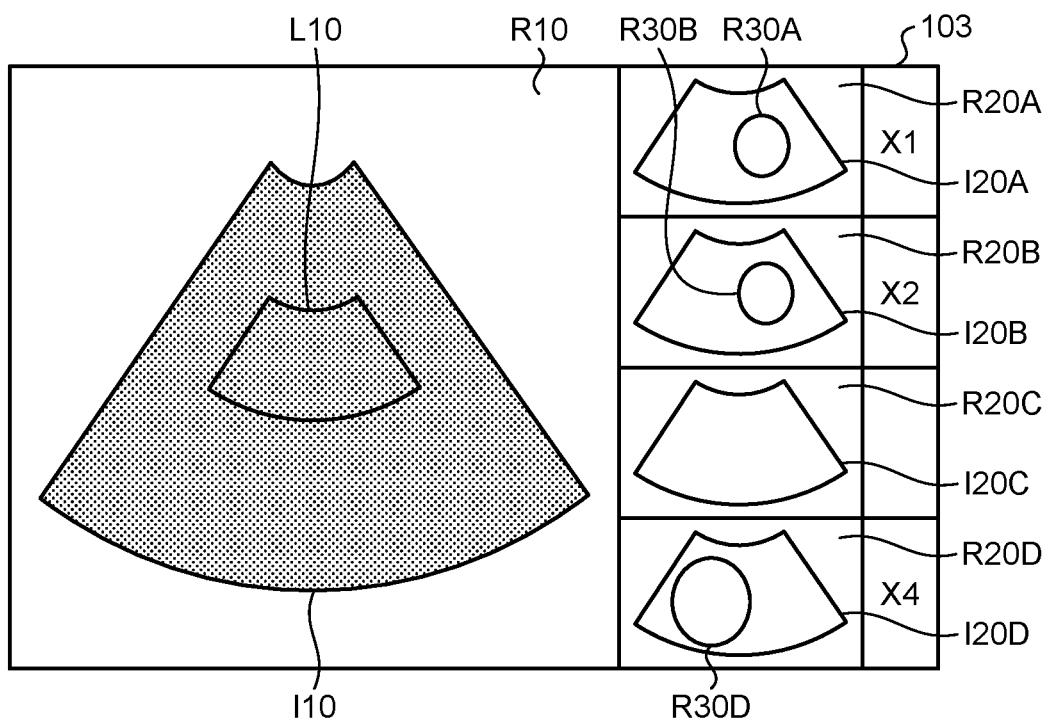
FIG. 6 is a diagram illustrating an example of a display screen according to a second modified example of the embodiment.

FIG. 6 is a diagram illustrating an example of a display screen according to a second modified example of the embodiment. As illustrated in FIG. 6, the display control function 163 displays three measurement regions R30A, R30B, and R30D. Specifically, the measurement region R30A is displayed in the analytical image I20A. The measurement region R30B is displayed in the analytical image I20B. The measurement region R30D is displayed in the analytical image I20D. Because measurement is not conducted for the analytical image I20C in the example of FIG. 6, a measurement region and a measured value are not displayed for the analytical image I20C.

The measurement regions R30A and R30B have their positions and sizes in common with each other. That is, if the position or size of any one of the measurement regions R30A and R30B is changed by an operator, that change is reflected in the position or size of the other one in synchronization. Accordingly, the types of analytical images to have their measurement regions in common with one another may be determined beforehand or may be specified by an operator each time. For example, plural analytical images generated by the same ultrasound scan preferably have their measurement regions in common.

Third Modified Example

An analytical image corresponding to an ROI (the frame line L10) displayed in the first display region may be displayed inside the ROI (the frame line L10), for example.

FIG. 7 is a diagram illustrating an example of a display screen according to a third modified example of the embodiment. The upper display screen in FIG. 7 is the same as the display screen in FIG. 3.

As illustrated by the upper display screen in FIG. 7, an operator executes an operation (interchanging operation) for interchanging the frame line L10 with the analytical image I20A (a double-headed dashed arrow in FIG. 7). This operation is executed by, for example, a drag-and-drop operation for an analytical image to be interchanged, to the first display region. This operation causes the display control function 163 to display the analytical image I20A at a position corresponding to the frame line L10 in the first display region as illustrated by the lower display screen in FIG. 7. Furthermore, the display control function 163 causes an image corresponding to the inside of the frame line L10 of the B-mode image, to be displayed at the position of the analytical image I20A in the second display region. The operation may cause the display control function 163 to display the representative value X1 corresponding to the analytical image I20A to be displayed in the first display region and cause the location where the representative value X1 was being displayed before the operation to be blank.

That is, according to an operation from an operator, the display control function 163 causes one of plural analytical images to be displayed at a position corresponding to an ROI of the morphology image. Furthermore, according to the operation from the operator, the display control function 163 causes an image that corresponds to the ROI and that is a part of the morphology image, to be displayed in one of plural second display regions.

Fourth Modified Example

A combined image formed of any images selected from plural analytical images may be displayed in a second display region, for example.

FIG. 8 is a diagram illustrating an example of a display screen according to a fourth modified example of the embodiment. The upper display screen in FIG. 8 is the same as the display screen in FIG. 3.

As illustrated by the upper display screen in FIG. 8, an operator executes (a dashed arrow in FIG. 8) an operation (combining operation) for combining the analytical image I20B with the analytical image I20C. This operation is executed by, for example, a drag-and-drop operation of one of the analytical images to be combined, to the other one of the analytical images to be combined. This operation causes the display control function 163 to display a combined image I20F in the second display region R20C as illustrated by the lower display screen in FIG. 8. The combined image I20F may be generated by any combining method. For example, the combined image I20F may be generated by superimposing the analytical image I20B and the analytical image I20C on each other in a state where the transparency of at least one of the analytical image I20B and the analytical image I20C has been changed, or may be generated by superimposing the analytical image I20B and analytical image I20C on each other in a state where at least one of the hue, chroma, and brightness of at least one of the analytical image I20B and the analytical image I20C has been changed.

That is, plural analytical images displayed in plural second display regions include at least two of: a first image corresponding to a first parameter; a second image corresponding to a second parameter different from the first parameter; a third image (a combined image) corresponding to the first parameter and the second parameter; and a fourth image that corresponds to a region of interest and is a part of the morphology image. The first parameter and the second parameter are parameters related to a tissue characteristic, bloodstream, or quality. That is, the display control function 163 displays the combined image that is a combination of at least two of the plural images, at a position corresponding to the region of interest of the morphology image or in a second display region.

Furthermore, according to an operation by an operator, the display control function 163 may execute processing for returning the combined image to its original analytical images. For example, in the example illustrated in FIG. 8, when an operator presses a cancel button B10, the display control function 163 may separate the combined image I20F into the analytical image I20B and the analytical image I20C. In the example illustrated in FIG. 8, the cancel button B10 is arranged in the first display region R10, but the cancel button B10 may be arranged inside or near the region in which the combined image I20F is displayed.

FIG. 8 corresponds to a case where the analytical images that have been combined are not displayed, but the embodiment is not limited to this case. For example, the display control function 163 may separately provide a new second display region while still displaying the analytical image I20B and the analytical image I20C that have been combined, respectively in their second display regions, and display the combined image in that new second display region. Furthermore, the display control function 163 may display the combined image in the first display region.

FIG. 8 corresponds to a case where analytical images are combined together but the embodiment is not limited to this case. An image to be combined with another image may be a B-mode image. If a B-mode image is to be combined with another image, a contour image illustrating contours of tissue extracted from the B-mode image may be combined with the B-mode image.

FIG. 8 corresponds to a case where a combined image is generated according to an operation by an operator, but the embodiment is not limited to this case. For example, generation and display of a combined image may be executed as a routine process according to a predetermined layout rule.

Fifth Modified Example

With respect to the embodiment, the case where an elasticity image, a viscosity image, and a quality image are collected by the same ultrasound scan has been described, for example, but the embodiment is not limited to this case. For example, the ultrasound diagnosis apparatus 1 may execute a series of ultrasound scans for obtaining a medium to high velocity bloodstream image, a low velocity bloodstream image, and a B-mode image.

Figure 9:
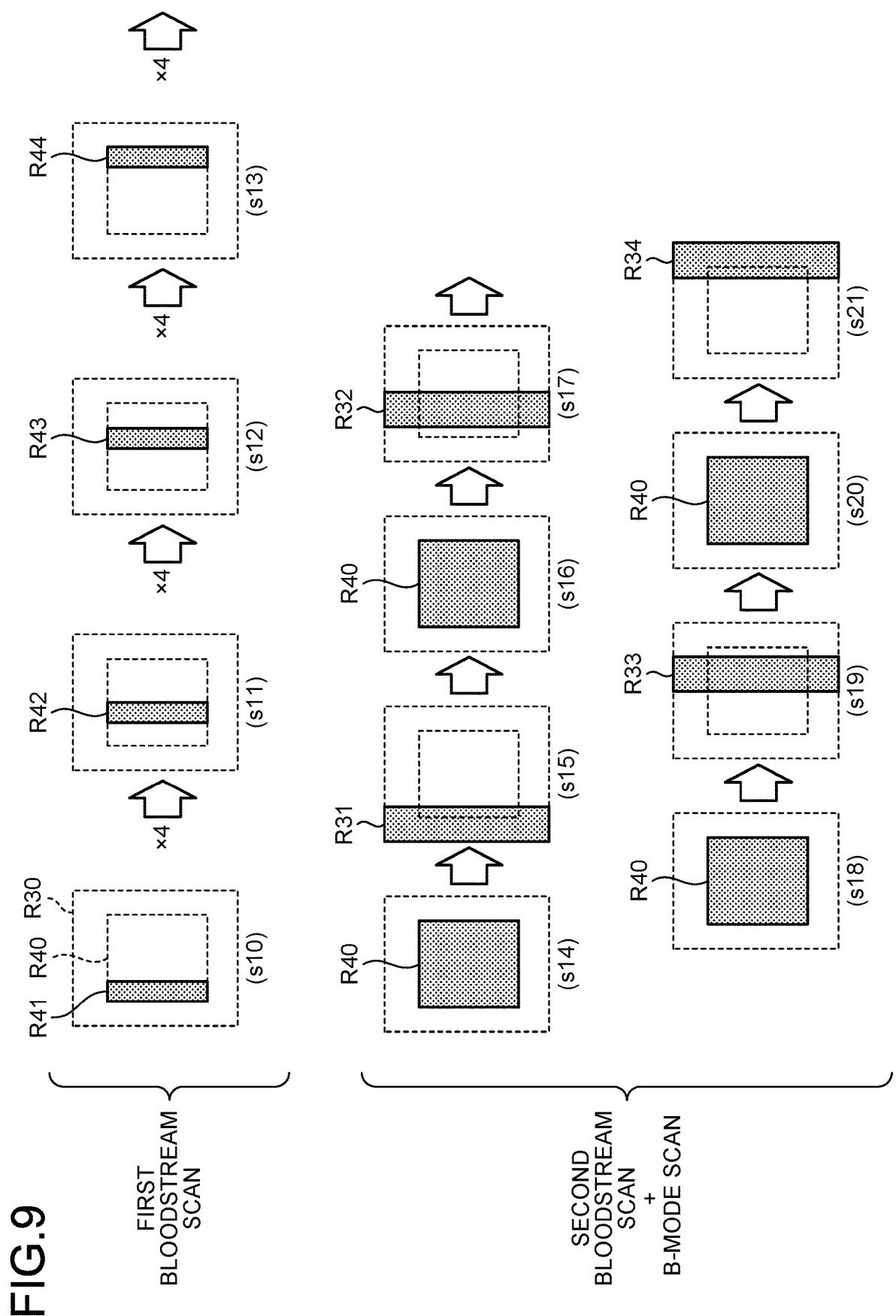
FIG. 9 is a diagram illustrating an example of ultrasound scans according to a fifth modified example of the embodiment.

FIG. 9 is a diagram illustrating an example of ultrasound scans according to a fifth modified example of the embodiment. A case where, as a series of ultrasound scans, a first bloodstream scan for collecting a medium to high velocity bloodstream image, a second bloodstream scan for collecting a low velocity bloodstream image, and a B-mode scan for collecting a B-mode image are executed will be described by reference to FIG. 9. In FIG. 9, s10 to s21 correspond to ultrasound scans for collecting a medium to high velocity bloodstream image, a low velocity bloodstream image, and a B-mode image for an n-th frame. Furthermore, a region R30 corresponds to a scan range (FOV) for the B-mode image. Four regions R31, R32, R33, and R34 correspond respectively to regions resulting from division of the region R20 into four along the azimuth direction. Furthermore, a region R40 corresponds to a scan range (ROI) of the medium to high velocity bloodstream image and low velocity bloodstream image. In addition, four regions R41, R42, R43, and R44 correspond respectively to regions resulting from division of the region R40 into four along the azimuth direction.

As illustrated in FIG. 9, the transmitting and receiving circuitry 110 firstly executes the first blood stream scan for the region R41 four times (s10). A data string having a data length, "4", is obtained for each position included in the region R41 by these four first bloodstream scans. The signal processing circuitry 120 collects medium to high velocity bloodstream information corresponding to the region R41 by executing, for each position included in the region R41, filtering processing on the data string for the same position.

Subsequently, the transmitting and receiving circuitry 110 executes the first bloodstream scan four times for each of the regions R42, R43, and R44, similarly to that for the region R41 (s11, s12, and s13). For the regions R42, R43, and R44 also, similarly to the region R41, the signal processing circuitry 120 collects medium to high velocity bloodstream information corresponding to the regions R42, R43, and R44 by executing, for each position included in each region, filtering processing on the data string for the same position. This medium to high velocity bloodstream information is an example of "first bloodstream information related to a first bloodstream velocity".

That is, through the ultrasound scans of s10 to s13, the signal processing circuitry 120 collects medium to high velocity bloodstream information corresponding to the region R40. By assigning a pixel value according to the medium to high velocity bloodstream information to each position in the region R40, the image processing circuitry 130 generates the medium to high velocity bloodstream image of the n-th frame.

Next, the transmitting and receiving circuitry 110 executes B-mode scans for the regions R31, R32, R33, and R34 in a time-division manner between second bloodstream scans for the region R40. Specifically, the transmitting and receiving circuitry 110 executes a second bloodstream scan for the region 40 once (s14). Subsequently, the transmitting and receiving circuitry 110 executes a B-mode scan for the region R31 once (s15). The transmitting and receiving circuitry 110 then executes a second bloodstream scan for the region R40 once (s16). Subsequently, the transmitting and receiving circuitry 110 executes a B-mode scan for the region R32 once (s17). The transmitting and receiving circuitry 110 then executes a second bloodstream scan for the region R40 once (s18). Subsequently, the transmitting and receiving circuitry 110 executes a B-mode scan for the region R33 once (s19). The transmitting and receiving circuitry 110 then executes a second bloodstream scan for the region R40 once (s20). Subsequently, the transmitting and receiving circuitry 110 executes a B-mode scan for the region R34 once (s21).

A data string having a data length, "4", is obtained for each position included in the region R40 through the four second bloodstream scans at s14, s16, s18, and s20. Because the B-mode scans are inserted in a time-division manner between the data sets for the data strings collected by the second bloodstream scans, the time intervals between the samples are longer than those between the data strings collected by the first bloodstream scans. Therefore, the data strings collected by the second bloodstream scans enable obtainment of information on bloodstream having a lower velocity than that obtained from the data strings collected by the first bloodstream scans. That is, the signal processing circuitry 120 collects low velocity bloodstream information corresponding to the region R40 by executing, for each position included in the region R40, filtering processing on the data string for the same position. This low velocity bloodstream information is an example of "second bloodstream information related to a second bloodstream velocity lower than the first bloodstream velocity".

The image processing circuitry 130 then generates the low velocity bloodstream image of the n-th frame by assigning pixel values according to the low velocity bloodstream information respectively to positions in the region R40.

Furthermore, B-mode data corresponding to the region R30 are able to be obtained through the four B-mode scans at s15, s17, s19, and s21. The image processing circuitry 130 generates the B-mode image of the n-th frame by assigning pixel values according to the B-mode data respectively to positions in the region R30.

As described above, the transmitting and receiving circuitry 110 executes, in a time-division manner, B-mode scans between second bloodstream scans when executing a series of ultrasound scans including first bloodstream scans, the second bloodstream scans, and the B-mode scans. The ultrasound diagnosis apparatus 1 is thereby able to execute a series of ultrasound scans for obtaining a medium to high velocity bloodstream image, a low velocity bloodstream image, and a B-mode image.

That is, in the fifth modified example, the first parameter is a parameter related to the first bloodstream velocity, and the second parameter is a parameter related to the second bloodstream velocity lower than the first bloodstream velocity.

The description related to FIG. 9 is just an example, and is not limited to the illustration in FIG. 9. For example, the data lengths of the data strings are not necessarily "4", and any number may be set as the data length. Furthermore, the number of divisions of each region is not necessarily "4", and may be set at any number.

Furthermore, examples of images collected by the same (common) ultrasound scan are not limited to a combination of an elasticity image, a viscosity image, and a quality image, nor a combination of a medium to high velocity bloodstream image, a low velocity bloodstream image, and a B-mode image. For example, an attenuation image may be collected by an ultrasound scan in common with a B-mode image. That is, if a first image is an attenuation image, the transmitting and receiving circuitry 110 executes a series of ultrasound scans including an ultrasound scan for obtaining the morphology image and a first image and an ultrasound scan for obtaining a second image.

Other Embodiments

Various different embodiments may be adopted in addition to the embodiment described above.

Enlargement, Reduction, and Parallel Translation

For example, the display range of an analytical image may be configured to be movable by an operation, such as scrolling or panning. In this case, a frame line indicating this display range is preferably displayed, separately from a frame line indicating an ROI, on a B-mode image displayed in a first display region, Furthermore, the display control function 163 executes enlargement, reduction, or parallel translation of plural analytical images in synchronization with one another according to an operation by an operator. For example, when any of the analytical images is enlarged, reduced, or parallel-translated according to an operation by an operator, the display control function 163 applies processing corresponding to the operation similarly to the other analytical images.

Processing when ROI is not Set

In a case where setting of an ROI is not essential for analysis, for example, in a case where a parameter to be analyzed is a value representing uniformity of speckles in a B-mode image (for example, a value resulting from normalization of dispersed values of brightness per local region in a B-mode image), an ROI may be automatically set with reference to the center of the FOV, for example. In that case, the display control function 163 causes the image included in the ROI automatically set, to be displayed in a second display region. The value representing uniformity of speckles in the B-mode image may be calculated by setting a region of interest.

Display of Information Other than Images

Information other than a medical image, for example, a radar chart comprehensively representing measured values for plural parameters, or a graph representing temporal change in measured values, may also be displayed in a second display region. Furthermore, for example, information other than a medical image, for example, a radar chart comprehensively representing measured values for plural parameters, or a graph representing temporal change in measured values, may also be displayed in a first display region.

Image Processing Apparatus

An ultrasound diagnosis apparatus has been described above with respect to the embodiment, but the embodiment is not limited to ultrasound diagnosis apparatuses. For example, the above described processing according to the embodiment may be executed by an image processing apparatus that is capable of processing information (ultrasound images and/or scan data) collected by the ultrasound diagnosis apparatus 1, the image processing apparatus being, for example, a personal computer or a work station.

In that case, the image processing apparatus includes an input interface, a display, a storage, and processing circuitry. The input interface, the display, the storage, and the processing circuitry included in the image processing apparatus are basically the same as the input interface 102, the display 103, the storage 150, and the processing circuitry 160 described by reference to FIG. 1, and description thereof will thus be omitted.

In this image processing apparatus, the processing circuitry receives (obtains) information collected by the ultrasound diagnosis apparatus 1, from the ultrasound diagnosis apparatus 1. The processing circuitry has at least a display control function similar to the display control function 163. This display control function is basically the same as the display control function 163 and description thereof will thus be omitted. The image processing apparatus thereby enables improvement in browsability of images, similarly to the ultrasound diagnosis apparatus 1 described above.

When the embodiment is applied to the image processing apparatus, images to be processed are not necessarily ultrasound images. For example, the images to be processed may be medical images captured by any medical diagnostic imaging apparatus, such as CT images captured by an X-ray computed tomography (CT) apparatus or MR images captured by a magnetic resonance imaging (MRI) apparatus. Examples of the medical diagnostic imaging apparatus include an X-ray diagnostic apparatus, an X-ray CT apparatus, an MRI apparatus, a single photon emission computed tomography (SPECT) apparatus, a positron emission computed tomography (PET) apparatus, a SPECT-CT apparatus having a SPECT apparatus and an X-ray CT apparatus integrated together, a PET-CT apparatus having a PET apparatus and an X-ray CT apparatus integrated together, and a group of any of these apparatuses.

Dual Monitoring Function

The embodiment described above is also applicable to a dual monitoring function for using two monitors (display 103) in combination.

Figure 10:
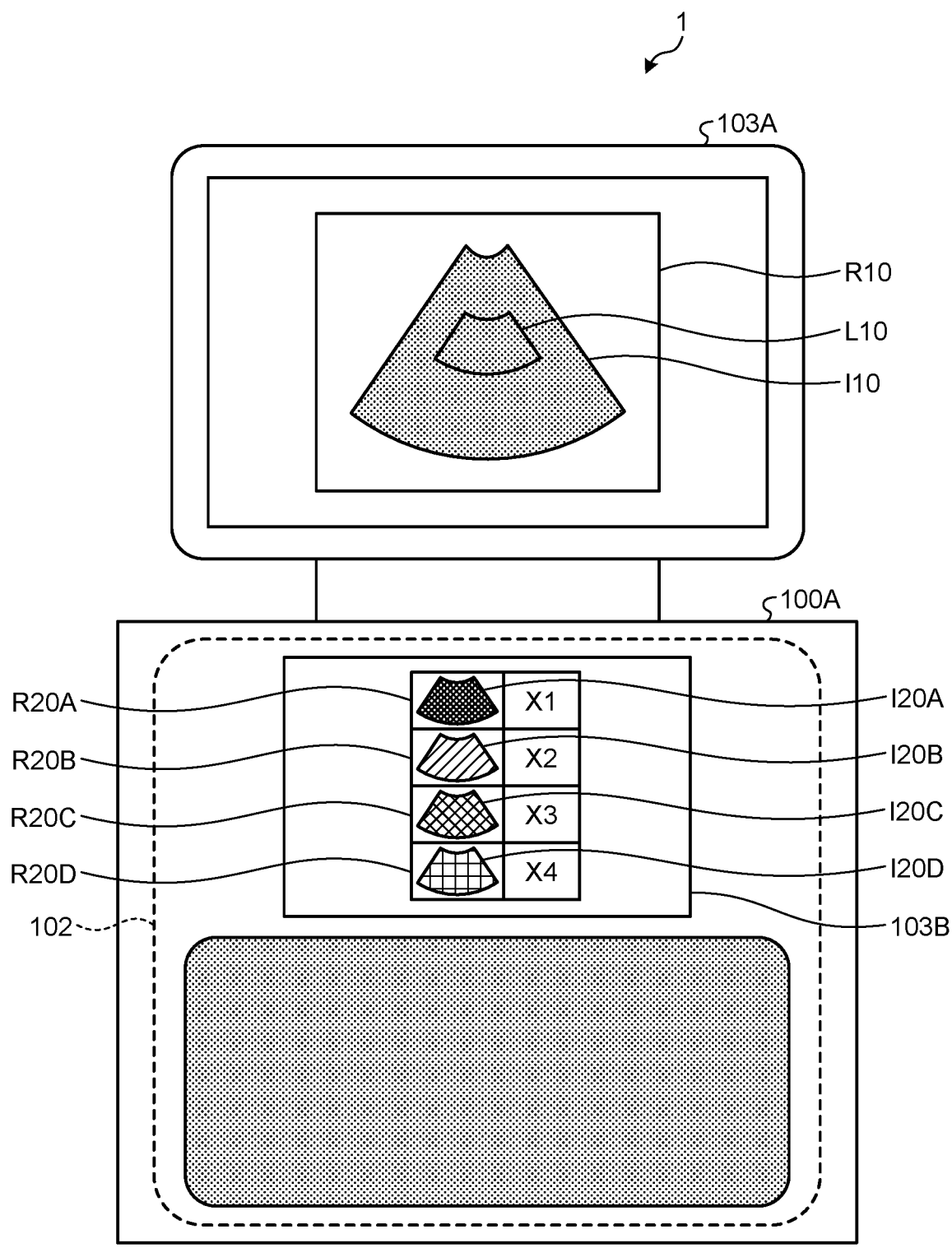
FIG. 10 is a diagram for explanation of a case where a dual monitoring function is applied to the ultrasound diagnosis apparatus according to the embodiment.

A case where the dual monitoring function is applied to the ultrasound diagnosis apparatus 1 according to the embodiment will be described using FIG. 10. FIG. 10 is a diagram for explanation of the case where the dual monitoring function is applied to the ultrasound diagnosis apparatus 1 according to the embodiment.

As illustrated in FIG. 10, the ultrasound diagnosis apparatus 1 includes, as a display 103, a display 103A and a display 103B. The display 103A and the display 103B function as a dual monitor. For example, the display 103A has a display screen larger than a display screen of the display 103B.

The display 103A is a main display and is basically the same as the display 103 described above with respect to the embodiment. The display 103A is an example of a first display.

The display 103B is a touch panel display provided on a console 100A. The display 103B is a touch panel that has a display function similar to that of the display 103 and receives a contact operation (touch operation) by an operator. That is, the display 103B is provided on the console 100A as an input interface 102 that receives various setting requests from the operator. The display 103B is an example of a second display. The function for receiving the contact operation is also called a position input function or a touch panel function.

The display control function 163 causes a first display region R10 to be displayed on the display 103A. A B-mode image I10 and a frame line L10 are displayed in the first display region R10. The B-mode image I10 and the frame line L10 are the same as those described by reference to FIG. 3.

Furthermore, the display control function 163 causes four second display regions R20A, R20B, R20C, and R20D to be displayed in the "single vertical line form" on the display 103B. Furthermore, the display control function 163 causes four analytical images I20A, I20B, I20C, and I20D to be respectively displayed in the four second display regions R20A, R20B, R20C, and R20D. The display control function 163 also causes four values X1, X2, X3, and X4 to be respectively displayed inside or near the four second display regions R20A, R20B, R20C, and R20D. The second display regions R20A, R20B, R20C, and R20D, the analytical images I20A, I20B, I20C, and I20D, and the values X1, X2, X3, and X4 are the same as those described by reference to FIG. 3.

As described above, the display control function 163 causes a first display region to be displayed on a first display and plural second display regions to be displayed on a second display different from the first display. Therefore, the ultrasound diagnosis apparatus 1 displays analytical images close to each other (for example, in one line), and thus enables reduction in the distance of movement of an analyst's line of sight and improvement in browsability.

Furthermore, the display control function 163 causes the plural second display regions to be displayed on the display 103B having the touch panel function. An operator is thereby able to perform an operation for interchanging analytical images (third modified example) or an operation for combining analytical images (fourth modified example) through a touch operation, and convenient and intuitive operations are thus enabled.

The description related to FIG. 10 is just an example, and is not limited to the illustration in FIG. 10. For example, the dual monitoring function described by reference to FIG. 10 may be implemented in combination with any of the above described embodiment and modified examples as appropriate.

Furthermore, for example, the display control function 163 may cause the four second display regions R20A, R20B, R20C, and R20D to be displayed on the display 103A and the first display region R10 to be displayed on the display 103B.

Furthermore, by reference to FIG. 10, the case where one of the two monitors forming the dual monitor has the touch panel function has been described, but the dual monitor is not limited to this configuration. The two monitors forming the dual monitor may both have the touch panel function, or may both be without the touch panel function.

Furthermore, by reference to FIG. 10, the case where the dual monitoring function is applied to an ultrasound diagnosis apparatus has been described, but the application is not limited to this case. For example, in a case where the above described processing according to the embodiment is executed at an image processing apparatus, the dual monitoring function may also be applied to the image processing apparatus.

Furthermore, the components of the apparatuses have been functionally and conceptually illustrated in the drawings and are not necessarily configured physically as illustrated in the drawings. That is, specific modes of distribution and integration of the apparatuses are not limited to those illustrated in the drawings, and all or a part of each apparatus may be configured to be distributed or integrated functionally or physically in any units, according to various loads and/or use situations, for example. In addition, all or any part of the processing functions executed in the apparatuses may be implemented by a CPU and a program analyzed and executed by the CPU, or implemented as hardware by wired logic.

Furthermore, of the processing described with respect to the embodiment and modified examples described above, all or a part of the processing described as being performed automatically may be performed manually, or all or a part of the processing described as being performed manually may be performed automatically by a publicly known method. The processing procedures, control procedures, specific names, and information including various data and parameters, which have been described above and illustrated in the drawings may be modified in any way except otherwise described specifically.

Furthermore, any image processing method described above with respect to the embodiment and modified examples may be implemented by being executed by a computer, such as a personal computer or a work station, executing an image processing program that has been prepared beforehand. This image processing program may be distributed via a network, such as the Internet. Furthermore, this image processing program may be recorded in a computer-readable non-transitory recording medium, such as a hard disk, a flexible disk (FD), a CD-ROM, an MO, or a DVD, and executed by being read by a computer from the recording medium.

At least one of the embodiments described above enables improvement in browsability of images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
   processing circuitry configured to
      obtain a morphology image obtained by an ultrasound scan or ultrasound scans and plural images, each of the plural images corresponding to a region of interest in the morphology image and being based on a parameter different from a parameter of the morphology image;
      cause the morphology image to be displayed in a first display region; and
      cause the plural images to be displayed in respective plural second display regions that have been arranged in a predetermined display layout, each of the plural second display regions being smaller than the first display region and not being superimposed on the first display region.

2. The ultrasound diagnosis apparatus according to claim 1, wherein the plural images caused to be displayed by the processing circuitry include at least two of:
   a first image corresponding to a first parameter;
   a second image corresponding to a second parameter different from the first parameter;
   a third image corresponding to the first parameter and the second parameter; and
   a fourth image that corresponds to the region of interest and is a part of the morphology image.

3. The ultrasound diagnosis apparatus according to claim 2, further comprising:
   scan circuitry configured to execute a series of ultrasound scans including a first ultrasound scan for obtaining the morphology image, and a second ultrasound scan for obtaining the first image and the second image.

4. The ultrasound diagnosis apparatus according to claim 2, further comprising:
   scan circuitry configured to execute a series of ultrasound scans including a first ultrasound scan for obtaining the morphology image, a second ultrasound scan for obtaining the first image, and a third ultrasound scan for obtaining the second image.

5. The ultrasound diagnosis apparatus according to claim 2, further comprising:
   scan circuitry configured to execute a series of ultrasound scans including a first ultrasound scan for obtaining the morphology image and the first image, and a second ultrasound scan for obtaining the second image.

6. The ultrasound diagnosis apparatus according to claim 2, wherein
   the first parameter is a parameter related to an elasticity of tissue, a viscosity of tissue, an attenuation of ultrasound, a quality of the second parameter, a low velocity bloodstream, a high velocity bloodstream, or a temporal change in echo intensity, and
   the second parameter is a parameter related to the elasticity of tissue, the viscosity of tissue, the attenuation of ultrasound, the quality of the second parameter, the low velocity bloodstream, the high velocity bloodstream, or the temporal change in echo intensity.

7. The ultrasound diagnosis apparatus according to claim 2, wherein the processing circuitry is further configured to determine a display order for the plural images displayed in the second display regions, based on respective degrees of priority of the first parameter and the second parameter.

8. The ultrasound diagnosis apparatus according to claim 2, wherein the processing circuitry is further configured to display a combined image resulting from a combination of at least two of the plural images, in the second display region or at a position corresponding to the region of interest in the morphology image.

9. The ultrasound diagnosis apparatus according to claim 1, wherein the processing circuitry is further configured to cause a value to be displayed inside or around one of the plural second display regions, the value being obtained by measurement using an image corresponding to the one of the plural second display regions.

10. The ultrasound diagnosis apparatus according to claim 1, wherein the processing circuitry is further configured to cause an image to be displayed at a position corresponding to the region of interest in the morphology image, according to an operation by an operator, the image being any one of the plural images.

11. The ultrasound diagnosis apparatus according to claim 1, wherein the processing circuitry is further configured to cause an image to be displayed in any one of the plural second display regions, according to an operation by an operator, the image corresponding to the region of interest and being a part of the morphology image.

12. The ultrasound diagnosis apparatus according to claim 1, wherein the plural second display regions are arranged continuously or at intervals each narrower than a width of each of the second display regions along an arrangement direction of the second display regions.

13. The ultrasound diagnosis apparatus according to claim 1, wherein each of the plural images is an image corresponding to the region of interest, or an image limited to a region including the region of interest and smaller than a field of view of the morphology image.

14. The ultrasound diagnosis apparatus according to claim 1, wherein the processing circuitry is further configured to execute enlargement, reduction, or parallel translation of the plural images in synchronization with one another according to an operation by an operator.

15. The ultrasound diagnosis apparatus according to claim 1, wherein the processing circuitry is further configured to cause each image of the plural images to be displayed such that a depth direction of a scan line at a center of the image approximately coincides with a vertical direction on a screen.

16. The ultrasound diagnosis apparatus according to claim 1, wherein the processing circuitry is further configured to determine a display arrangement of the first display region and the plural second display regions, based on a number of the plural images corresponding to the region of interest.

17. The ultrasound diagnosis apparatus according to claim 1, wherein the processing circuitry is further configured to determine a display arrangement of the first display region and the plural second display regions, based on types of the images corresponding to the region of interest.

18. The ultrasound diagnosis apparatus according to claim 1, wherein
the processing circuitry is further configured to cause the first display region to be displayed on a first display and the plural second display regions to be displayed on a second display different from the first display,
the first display has a display screen larger than a display screen of the second display, and
the second display is a touch panel that receives a contact operation from an operator.

19. An image processing apparatus, comprising:
processing circuitry configured to
obtain a morphology image obtained by an ultrasound scan or ultrasound scans and plural images, each of the plural images corresponding to a region of interest in the morphology image and being based on a parameter different from a parameter of the morphology image;
cause the morphology image to be displayed in a first display region; and
cause the plural images to be displayed in respective plural second display regions that have been arranged in a predetermined display layout, each of the plural second display regions being smaller than the first display region and not being superimposed on the first display region.

* * * * *